United States Patent
Monos et al.

(10) Patent No.: US 12,178,618 B2
(45) Date of Patent: Dec. 31, 2024

(54) DETERMINATION OF SEPARATION DISTANCE FROM THERMAL AND ACOUSTIC INPUT

(71) Applicant: KYNDRYL, INC., New York, NY (US)

(72) Inventors: Harris Basil Monos, Melbourne (AU); Vicky A Rose, Hawthorn (AU); Elaheh ShafieiBavani, Melbourne (AU); Jorge Andres Moros Ortiz, Canberra (AU)

(73) Assignee: Kyndryl, Inc., New York, NY (US)

( * ) Notice: Subject to any disclaimer, the term of this patent is extended or adjusted under 35 U.S.C. 154(b) by 694 days.

(21) Appl. No.: 17/345,108

(22) Filed: Jun. 11, 2021

(65) Prior Publication Data
US 2022/0395234 A1    Dec. 15, 2022

(51) Int. Cl.
*A61B 5/01*    (2006.01)
*A61B 5/00*    (2006.01)
(Continued)

(52) U.S. Cl.
CPC ............ *A61B 5/7275* (2013.01); *A61B 5/015* (2013.01); *A61B 5/0823* (2013.01); *A61B 5/74* (2013.01);
(Continued)

(58) Field of Classification Search
CPC ..... A61B 5/7275; A61B 5/015; A61B 5/0823; A61B 5/74; A61B 2562/0204;
(Continued)

(56) References Cited

U.S. PATENT DOCUMENTS

| | | | |
|---|---|---|---|
| 10,009,579 B2 | 6/2018 | Wang | |
| 10,307,060 B2 | 6/2019 | Tran | |
| (Continued) | | | |

FOREIGN PATENT DOCUMENTS

| | | |
|---|---|---|
| CN | 103329135 B | 9/2013 |
| JP | 2006264461 A | 10/2006 |
| JP | 2017188052 A | 10/2017 |

OTHER PUBLICATIONS

Prather, Kimberly A., Chia C. Wang, and Robert T. Schooley. "Reducing transmission of SARS-CoV-2." Science 368.6498 (2020): 1422-1424. (Year: 2020).*

(Continued)

*Primary Examiner* — James M Kish
*Assistant Examiner* — Paroma Mukhopadhyay
(74) *Attorney, Agent, or Firm* — Erik Swanson; Andrew D. Wright; Calderon Safran & Wright P.C.

(57) ABSTRACT

A method for dynamically determining a separation distance in which thermal images of a space are received that indicate a count and location of users within the space, temperature of the users within the space are received along with acoustic data from the users within the space, which is filtered to include specific symptom-related sounds and discard other sounds. The one or more processors generate a probability of a contagious infection of users within the space at a location determined by the thermal images, based on correlating the temperature and the acoustic data associated with the users within the space. A separation distance from the users within the space is calculated, based on the locations and the probabilities of infection of the users within the space, and a notification corresponding to the calculated separation distance is delivered to a protected user.

19 Claims, 3 Drawing Sheets

(51) Int. Cl.
*A61B 5/08* (2006.01)
*G01J 5/00* (2022.01)
*G06T 7/70* (2017.01)

(52) U.S. Cl.
CPC .............. *G01J 5/0025* (2013.01); *G06T 7/70* (2017.01); *A61B 2562/0204* (2013.01); *A61B 2562/0271* (2013.01); *G01J 2005/0077* (2013.01); *G06T 2207/10048* (2013.01); *G06T 2207/30004* (2013.01); *G06T 2207/30242* (2013.01)

(58) Field of Classification Search
CPC ............ A61B 2562/0271; G01J 5/0025; G01J 2005/0077; G06T 7/70; G06T 2207/10048; G06T 2207/30004; G06T 2207/30242
See application file for complete search history.

(56) References Cited

U.S. PATENT DOCUMENTS

| | | | |
|---|---|---|---|
| 11,504,011 B1* | 11/2022 | Jain | G06N 5/04 |
| 11,568,887 B1* | 1/2023 | Sarzen | G10L 25/66 |
| 2015/0126824 A1 | 5/2015 | Leboeuf | |
| 2020/0146557 A1* | 5/2020 | Cheung | A61B 5/7267 |
| 2021/0158966 A1* | 5/2021 | Ozaki | G16H 50/30 |
| 2021/0287798 A1* | 9/2021 | Peterson | A61B 5/7267 |
| 2021/0345887 A1* | 11/2021 | Bean | A61B 5/6833 |
| 2021/0353155 A1* | 11/2021 | Caplin | G01J 5/025 |
| 2021/0375117 A1* | 12/2021 | Updike | G08B 21/22 |
| 2021/0390804 A1* | 12/2021 | Rajamanickam | A61B 5/0008 |
| 2022/0034542 A1* | 2/2022 | Peters | F24F 11/0001 |
| 2022/0277764 A1* | 9/2022 | Ciliberti | G16H 40/67 |
| 2022/0313095 A1* | 10/2022 | Lichtensztein | A61B 5/0017 |
| 2022/0346651 A1* | 11/2022 | Kimura | A61B 5/7267 |

OTHER PUBLICATIONS

Oh, Ju Hyun, et al. "Fabrication of high-sensitivity skin-attachable temperature sensors with bioinspired microstructured adhesive." ACS applied materials & interfaces 10.8 (2018): 7263-7270. (Year: 2018).*

Amendola, S. A. R. A., et al. "Design, calibration and experimentation of an epidermal RFID sensor for remote temperature monitoring." IEEE Sensors Journal 16.19 (2016): 7250-7257. (Year: 2016).*

"Contextualized Wearable Notification Trigger Analysis", IP.com No. IPCOM000262485D, IP.com Electronic Publication Date: Jun. 4, 2020, 6 pps., <https://priorart.ip.com/IPCOM/000262485>.

"MEZO Smart Shopping Cart / Trolley Solution", Media Mea, © 2021, media mea, 3 pps., <https://mediamea.store/products/mezo-smart-shopping-cart-trolley-solution>.

"Occupancy and Risk-aware Queuing Method and System", IP.com No. IPCOM000262969D, IP.com Electronic Publication Date: Jul. 17, 2020, 5 pps., <https://priorart.ip.com/IPCOM/000262969>.

"Tag sensors", Grant Committee, EU Horizon 2020, Tag Sensors solution from TAG Sensors, 14 pps.,<https://tag-sensors.com/solution/>.

"User Health Aware seat Assignment system", IP.com No. IPCOM000261846D, IP.com Electronic Publication Date: Apr. 10, 2020, 6 pps., <https://priorart.ip.com/IPCOM/000261846>.

Abate, "Stanford engineers have developed wireless sensors that stick to the skin to track our health", Aug. 16, 2019, 2 pps., <https://news.stanford.edu/2019/08/16/wireless-sensors-stick-skin-track-health/>.

* cited by examiner

DETERMINATION OF SEPARATION DISTANCE FROM THERMAL AND ACOUSTIC INPUT

FIELD OF THE INVENTION

The present invention relates generally to the field of personal safety, and more particularly to dynamically determining distances to maintain within a defined space occupied by multiple users.

BACKGROUND OF THE INVENTION

Disease transmission between humans can occur by direct contact and indirect contact. A common method of indirect contact transmission is when infectious agents, such as bacteria and viruses, become airborne from an infected human and inhaled by another uninfected human. Infectious agents are propelled into the air by sneezing and coughing by the infected human and can often remain airborne for a period of time that depends on the droplet size of the propelled agent.

Acoustic data can be captured within a space having predetermined dimensions and filtered to yield specific frequency combinations and discarding all remaining sound content. In some cases, acoustic data of people in a defined space can be captured by microphones of each consenting individual's smart devices, which can be filtered to capture specific sounds and combinations and discard all other sounds. The captured acoustic data can be attributed to a particular, but anonymous user by association with the user's smart device.

Thermal imaging techniques are used in a variety of conditions and applications. For example, thermal imaging is used to determine relative differences in the heat produced by engines submitted to different conditions, electrical components under various usage conditions, and natural phenomena, such as monitoring a volcano over time. Thermal imaging can also be used to identify homeothermic animals from inanimate objects, such as identifying the presence of a human in low light or dark conditions. Thermal imaging is sensitive to the infrared signatures of humans and other warm-blooded animals produced by the heat of their bodies.

SUMMARY

Embodiments of the present invention disclose a method, computer program product, and system for dynamically determining a separation distance to maintain. The method provides for one or more processors to receive thermal images of a space of pre-determined dimensions, wherein the thermal images indicate a count and location of users within the space. The one or more processors receive a temperature of the users within the space. The one or more processors also receive acoustic data from the users within the space from acoustic microphones within the space, such that the acoustic data is filtered to include specific symptom-like sounds and discard other sounds. The one or more processors generate a probability of contagious infection of a first user of the users within the space at a location determined by the thermal images. The one or more processors calculate a distance to maintain from the users within the space for a second user, based on the probability of the contagious risk of the first user, a location of the protected user, and a location of the first user within the space, and the one or more processors deliver to the second user the calculated separation distance to maintain from the users within the space.

DETAILED DESCRIPTION

Figure 1:
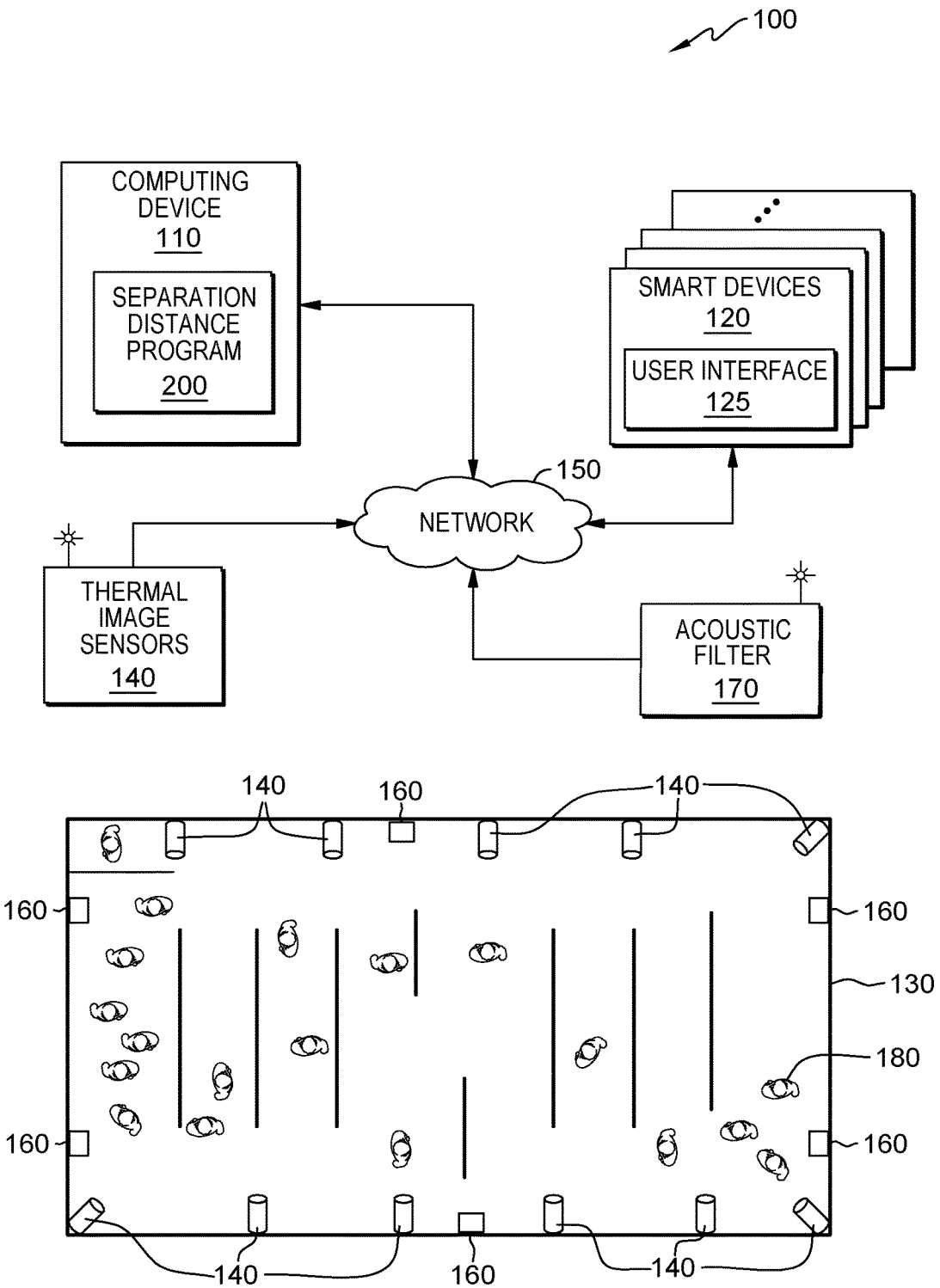
FIG. 1 is a functional block diagram illustrating a distributed data processing environment, in accordance with an embodiment of the present invention.

Embodiments of the present invention recognize that infectious diseases affecting human users can be transmitted between users by inhaling aerosol suspensions of the infectious agent in the air. Actions that produce extreme or excessive exhalation by an infected user that can produce the suspensions of the infection agents include coughing, sneezing, singing, yelling, extensive talking, and persistent deep exhaling. Embodiments recognize that recommended protection against transmission of infectious agents, such as bacteria and viruses, including maintaining a safe distance from potential sources of infection, among other recommendations. In some situations, certain indoor spaces include varying counts of users that dynamically change as the users move within the space, leave the space, and enter the space. Additionally, the density of users within sections of the indoor space can vary, due to gatherings, clustering of users in conversation, queues in a line, or other reasons.

Embodiments of the present invention also recognize that symptomatic users may display elevated temperatures and may produce coughs, sneezes, sniffling, or other actions that can be acoustically distinguished from other sounds and dialog. Determining users within a space that exhibit an elevated temperature and/or acoustically detecting users producing coughs, sneezes, and other sounds associated with an infectious condition, such as the flu or SARS-like infections, can contribute to determining a level of risk to a non-infected user entering the space.

Embodiments of the present invention recognize that professional medical organizations, such as the Center for Disease Control (CDC) and World Health Organization (WHO) provided direction of distances to maintain between users to reduce or avoid transmission of airborne and contact infectious exposure. In some embodiments, the recommended "safe distance" may increase if users in the immediate space are suspected or known to exhibit symptoms of infection. Thermal imaging to determine a count and location of users within a space or section of the space (supermarket aisles, airport, checkout lines, sporting events).

Embodiments of the present invention provide a method, computer program product, and computer system for dynamically determining a separation distance to maintain between users occupying a space, based on received input of dimensions and information regarding the space, input from thermal imaging sensors within the space, and acoustic data from smart devices of consenting users opting-in to the separation distance feature, and/or acoustic sensors within the space. The separation distance is calculated based on the quantity or count of users occupying the space, the density of the users within sections of the space, and the acoustic and temperature data associated with respective users within the space, and medical professional recommendations corresponding to the conditions dynamically determined for the user. Embodiments of the present invention present the separation distance radius to the participating user and indicate whether the user is at risk of violating the separation distance as the user navigates the space.

In embodiments, the dynamic determination of the separation distance to maintain is directed towards reducing or avoiding the transmission of infectious agents to a user enabled with an embodiment of the present invention within an indoor confined space. In embodiments, the space includes multiple users that move about within the space, such as in a store or an airport. In one embodiment, an administrator/controller role provides the input of the dimensions and additional information about the space. In other embodiments, software applications determined space dimensions by pixel analysis of camera images received and a known object and position within an image. The space dimensions and layout can further be customized for fixed (immovable) objects and fixtures, such as aisles within a store. In some embodiments, the space is monitored by multiple thermal cameras that produce composite views from which a count of users and the respective locations of the users within the space are determined, including the depth and distance between users and objects while actively moving throughout the space. Techniques using red, green, blue, depth images (RGB-D) can be applied to determine per-pixel depth information within images from thermal and visible light cameras positioned throughout the space.

In some embodiments, acoustic data is received by a computing system from acoustic capturing devices within the space. The acoustic data is filtered locally to anonymously include sounds associated with infectious symptoms, such as coughs, sneezes, clearing of a throat blowing the nose, and sniffles while filtering out additional sounds and dialog. In some embodiments, the filtering function is trained using artificial intelligence techniques, such as supervised machine learning in which a filtering model receives a multitude of acoustic sound examples of infectious disease symptoms as input along with data labeling the input. The model training also includes additional acoustic sounds that may include dialog, music, announcement sounds, mechanical sounds, and the like. In some embodiments, consenting users enable microphones on smart devices to detect sounds and transmit the sounds to the filtering model, which forwards the resulting symptom acoustic sounds to a receiving system, such as a computing device of a cloud platform. In some embodiments, additional acoustic sensors positioned at defined and known locations within the space serve to augment the collection of acoustic sound input and transmit the sounds to the filtering model, which forwards the resulting symptom acoustic sounds to the receiving system. In one embodiment, an application (app) operating on a consenting user's smart device performs the filtering of acoustic sounds, which prevents possible identifying data from being sent to the receiving computing system, which maintains anonymity.

In some embodiments of the present invention, the determination of the source of a received infectious symptom acoustic signal includes attributing the acoustic signal to the closest user as determined by algorithmically comparing the audio signal volume level across multiple devices that detect the acoustic sound. The user thermal image in closest proximity to the device(s) that records the greatest amplitude of the symptom acoustic sound is determined as the source. Additionally, the acoustic signal can be correlated with the thermal imagery to accurately determine the source of the acoustic signal by training the computing system of thermal images of coughing, sneezing, and other body movements associated with symptom acoustic sounds. The source user is indicated among the multiple users within the space without specifically identifying the user, which maintains the anonymity of embodiments. The identification of the acoustic symptom sound can be further combined with temperature data to complete a risk assessment for the user enabled with embodiments of the present invention.

In embodiments of the present invention, thermal imaging devices provide input used to determine the count of users within the space and to determine the relative density of users within sections of the space. In some embodiments, appropriately positioned thermal imaging cameras, such as elevated and along border walls of the space, provide coverage of all sections of the space indicating the number of users in the space, the location of respective users, and movement of users. Additionally, the thermal images received may provide temperature data of users, which may be based on the skin surfaces of the user or touch spots made by a user. The temperature data contributes to identifying users within the space that may be exhibiting symptoms of infectious disease and may present a risk to a user-enabled with embodiments of the present invention.

In one embodiment, contact stickers adhered to carts, baskets, or handles of other carrying devices, include temperature detection functionality and wireless transmission of the temperature data as a source of temperature data of users within the space. For example, users in a store often make use of carts, baskets, or bags to carry items to purchase. The handles of the carrying devices can be outfitted with flexible contact stickers that sense the contact temperature of the user and transmit the temperature data wirelessly to a receiving device. In some embodiments, the contact stickers include an identification that enables associating temperature data with a particular user's location within the space. Embodiments of the present invention maintain the anonymity of users while detecting and transmitting thermal and acoustic data associated with a plurality of users within the space.

The dynamic determination of separation distance objectives includes dependencies on the attributes of the space, the count and location of users within the space, and the detection of users displaying infectious disease symptoms. The determination of separation distance considers the space and occupying user data as well as the professional medical recommendations at the time as well as other factors related to the space being monitored such as ceiling height and ventilation. The data received by the system and interpreted in real-time allows for a fluid adaptation of a given radius around a user, which determines how many people should safely be in each area.

Based on the professional medical recommendation at the time for a "one-on-one" user interaction in an indoor space, a separation distance basis or starting point is provided to the system by an administrator/controller role and is updated as medical recommendations are updated. Separation distance adjustments are made based on the input data received that includes a count of users within the space, the location of users within sections of the space, and the probability of contagious infection determined by the medical professional information of presently known infections disease and detection of temperature and acoustic signals indicating potential infectious disease symptoms from specific users and the location of the users within the space. The adjustments to the separation distance increase as the user receiving protection from embodiments of the present invention (hereafter referred to as the protected user), approaches detected higher-risk conditions. The protected user's separation distance radius would be increased if users within the space and in the vicinity of the protected user show symptoms that could be potentially contagious. In some embodiments, the detection of users within the space that could be potentially contagious can activate a cleaning system of the space and inform other users to avoid or leave the section or aisle temporarily without revealing the source user. In some embodiments, the separation distance calculation exceeds a pre-determined threshold, and the protected user receives a notification to avoid entering the space.

The present invention will now be described in detail with reference to the Figures. FIG. 1 depicts a functional block diagram illustrating a distributed data processing environment, generally designated 100, in accordance with an embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes computing device 110, smart devices 120, thermal image sensors 140, acoustic sensors 160, and acoustic filter 170, all interconnected via network 150. Distributed data processing environment 100 also includes indoor space 130 and users 180. Network 150 can be, for example, a local area network (LAN), a wide area network (WAN), such as the Internet, a virtual local area network (VLAN), or any combination that can include wired, wireless, or optical connections. In general, network 150 can be any combination of connections and protocols that will support communication between computing device 110, smart devices 120, thermal image sensors 140, and acoustic filter 170.

Smart devices 120 collectively represent the smart devices of users 180 present within indoor space 130. Smart devices 120 include user interface 125, respectively, enabling users of smart devices 120 to access applications, communicate, and receive notifications and messages, such as notifications from separation distance program 200. In embodiments of the present invention, users of smart devices 120 have opted-in, providing consent to allow features of smart devices 120 to receive and transmit acoustic data detected within indoor space 130. In some embodiments, smart devices 120 include an app (not shown) to filter acoustic sounds at the local level of smart devices 120, and transmitting the acoustic sounds associated with infectious disease symptoms, such as a cough, a sneeze, blowing of the nose, and sniffling. In some embodiments, the acoustic data detected by acoustic sensors and smart devices 120 that are not configured to filter acoustic sounds locally on smart devices 120, are wirelessly transmitted to acoustic filter 170.

User interface 125 represents the respective user interfaces of smart devices 120. User interface 125 provides an interface for users to access the features and functions of smart devices 120. In some embodiments of the present invention, user interface 125 provides access to separation distance notifications to a protected user from separation distance program 200 and may support the training of a machine learning model to filter acoustic sounds from a component of separation distance program 200. User interface 125 may also provide access and operation controls of other applications, features, and functions of computing device 110 (not shown). In some embodiments, user interface 125 provides display output and input functions for computing device 110. In other embodiments, user interface 125 provides display output and enables the selection of options and functions associated with separation distance program 200 operating on respective devices of smart devices 120.

User interface 125 supports access to alerts, notifications, and provides access to forms of communications. In one embodiment, user interface 125 may be a graphical user interface (GUI) or web user interface (WUI) and can receive user input and display text, documents, web browser windows, user options, application interfaces, and instructions for operation, and include the information (such as graphic, text, and sound) that a program presents to a user and the control sequences the user employs to control the program. In another embodiment, user interface 125 may also include mobile application software that provides respective interfaces to features and functions of computing device 110. User interface 125 enables respective users of smart devices 120 to receive, view, hear, and respond to input, access applications, display content of online conversational exchanges, and perform available functions.

Indoor space 130 defines a volume of space that includes a dynamically changing count of users. In some embodiments, indoor space 130 includes dimensions known and provided by an administrator or controller role. In other embodiments, the dimensions of indoor space 130 may be determined by analysis of pixels of images taken from cameras mounted in various positions of indoor space 130. Indoor space 130 includes thermal image sensors 140, acoustic sensors 160, and users 180.

Thermal image sensors 140 include a plurality of sensors that provide input used to determine a count of users within indoor space 130. In some embodiments, thermal image sensors 140 provide thermal touch spot data of individual users that can be used to determine the respective user's temperature and contribute to determining whether the user poses a contagious risk of infectious disease. In some embodiments, thermal image sensors 140 are positioned throughout indoor space 130 enabling coverage of the floor area and sections of indoor space 130 separated by structure or objects. In some embodiments, thermal image sensors 140 transmit thermal image data wirelessly to separation distance program 200 operating on computing device 110 via network 150. The thermal image data enables the detection of a count of users within indoor space 130 without specifically performing an identification of the individual users.

Acoustic sensors 160 include a plurality of devices configured to receive acoustic signals (i.e., sounds) within a section of indoor space 130. Acoustic sensors 160 transmit the acoustic signals from specific defined and known locations within sections of indoor space 130 to separation distance program 200 operating on computing device 110. The signals transmitted by acoustic sensors 160 indicate an intensity of the received acoustic signals, which enables separation distance program 200 to assign acoustic sounds such as a cough, a sneeze, clearing of a throat, to a particular user based on the proximity of the user and the intensity of the acoustic signal received by respective sensors.

In some embodiments, the smart device microphones of users within indoor space 130 augment the detection of acoustic signals by acoustic sensors 160, such that the users have consented to the use of the smart device data collection to support notification receipt from separation distance program 200. In some embodiments, acoustic sensors 160 receive acoustic signals as data and transmit the data wirelessly to acoustic filter 170, which filters the input to include only the acoustic signals corresponding to sounds associated with a potentially contagious user, discarding other acoustic input. In other embodiments, the filtering of the acoustic signals received as data occurs locally with acoustic sensors 160, and transmission of the filtered acoustic data includes only the sounds associated with users that are potentially contagious.

Acoustic filter 170 receives acoustic signal data from acoustic sensors 160 distributed throughout indoor space 130 and filters the acoustic signals such that sounds associated with a user exhibiting symptoms of a potentially contagious disease (i.e. flu, SARS-like, etc.) and discards other acoustic sounds received. Acoustic filter 170 maintains an anonymous collection of acoustic sounds and protects the privacy of users within indoor space 130. In some embodiments, acoustic filter 170 performs as a separate device that receives acoustic signals from acoustic sensors 160 and transmits the filtered acoustic signals to separation distance program 200 operating on computing device 110. In other embodiments, acoustic filter 170 functions as a component within acoustic sensors 160 (not shown) and performs locally in user smart devices that include application (app) function to filter the received acoustic sounds locally and transmit the resulting filtered acoustic data to separation distance program 200 via network 150.

The small circular objects in FIG. 1 represent users within indoor space 130, identified by labeling of one such user as users 180. In embodiments of the present invention, users in indoor space 130 move dynamically and dynamically generate acoustic sound data. The locations and density of all users, such as users 180, within indoor space 130 are determined by separation distance program 200, based on thermal imaging received from thermal image sensors 140. The use of thermal images provides anonymity to the users within indoor space 130 while providing a count and location of the users.

In one embodiment, computing device 110 hosts operation of separation distance program 200. In some embodiments, computing device 110 can be a blade server, a web server, a laptop computer, a desktop computer, a standalone mobile computing device, a smartphone, a tablet computer, or another electronic device or computing system capable of receiving, sending, and processing data. In other embodiments, computing device 110 may be a computing device interacting with applications and services hosted and operating in a cloud computing environment. In another embodiment, the computing device 110 can be a netbook computer, a personal digital assistant (PDA), or other programmable electronic devices capable of receiving data from and communicating with other devices (shown and not shown) in distributed computer processing environment 100, via network 150, as well as performing operations of separation distance program 200. Alternatively, in some embodiments, computing device 110 may be communicatively connected to separation distance program 200, operating remotely. Computing device 110 may include internal and external hardware components, depicted in more detail in FIG. 3.

Separation distance program 200 receives thermal images from thermal image sensors 140 and acoustic data from acoustic sensors 160 and processed through acoustic filter 170 for indoor space 130. Separation distance program 200 determines the count and density of users within indoor space 130, based on the thermal image data in which the density of users includes determining the count and proximity of users within a particular section within indoor space 130. The thermal image associated with a respective user of users 180 within indoor space 130 is used to associate user temperature and acoustic sounds indicating potential symptoms of a contagious infection of the user.

Separation distance program 200 receives acoustic data from acoustic sensors 160 subsequent to the processing of the acoustic data through acoustic filter 170. In some embodiments, acoustic signal data from smart device microphones of opted-in users 180 augment the acoustic data from acoustic sensors 160. Separation distance program 200 dynamically determines a distance for the protected user to maintain as the protected user enters indoor space 130 and navigates within indoor space 130, based on the count and location of the users determined by the thermal image data and based on determining the potential contagious risk presented by respective users within indoor space 130 by the temperature data and acoustic signal data received. As the location of the protected user changes along with the location, count, and potential contagious indications of the users within indoor space 130 change, the separation distance presented to the protected user changes.

In some embodiments of the present invention, thermal strips attached to handles of carts, bags, or other carrying devices register user thermal touch temperatures that correlate to the respective user's body temperature, which may indicate a symptom of a contagious condition. The thermal strips transmit a wireless signal that indicates a temperature associated with a particular user. In some embodiments, the detected temperatures of users within indoor space 130 are optionally or additionally detected by touch temperatures of the users detected by thermal image sensors on objects handled within indoor space 130.

Some variables considered in determining the separation distance, and which can be configurable by the system administrator/controller, include the indoor space and separation distance objectives, with dependency on the professional medical advice at the time regarding a separation distance under known conditions. The aggregation of anonymous thermal image sensors and filtered acoustic data enables a calculatable distance between other users. A system administrator's input guided by professional medical advice or defaulted to a standard medical practitioner 2-meter rule, determines a radius around the protected user, based on the detection of contagious symptom acoustic sounds and the number and density of anonymous users in the space.

For example, a longer separation distance to maintain is provided to the protected user in a space that includes users with symptoms of potential infection, and the protected user receives a notification to maintain a shorter separation distance under conditions in which a lower count of users that have an absence of contagious symptoms reside in the general vicinity of the protected user. In some embodiments, the determination of a separation distance includes other factors related to the space being monitored, such as ceiling height and ventilation which are known to the administrator/controller. The dynamic receipt of the input data, interpreted in real-time, allows for a fluid adaptation of a given radius around the protected user. The radius of separation distance around the protected user informs how many people should safely be in a given area or section of the indoor space. If the other users within the indoor space show symptoms that could indicate potential contagious conditions, the user's radius would be increased. In some embodiments, the determination of a longer or increasing radius of separation distance around the protected user may also activate a cleaning or sterilizing action in the space and may also provide notification to other users to avoid or leave a section of the space temporarily without revealing the potentially contagious source user. In some embodiments, the protected user may be notified to not enter the indoor space due to conditions that limit or prevent maintaining an acceptable separation distance.

Figure 2:
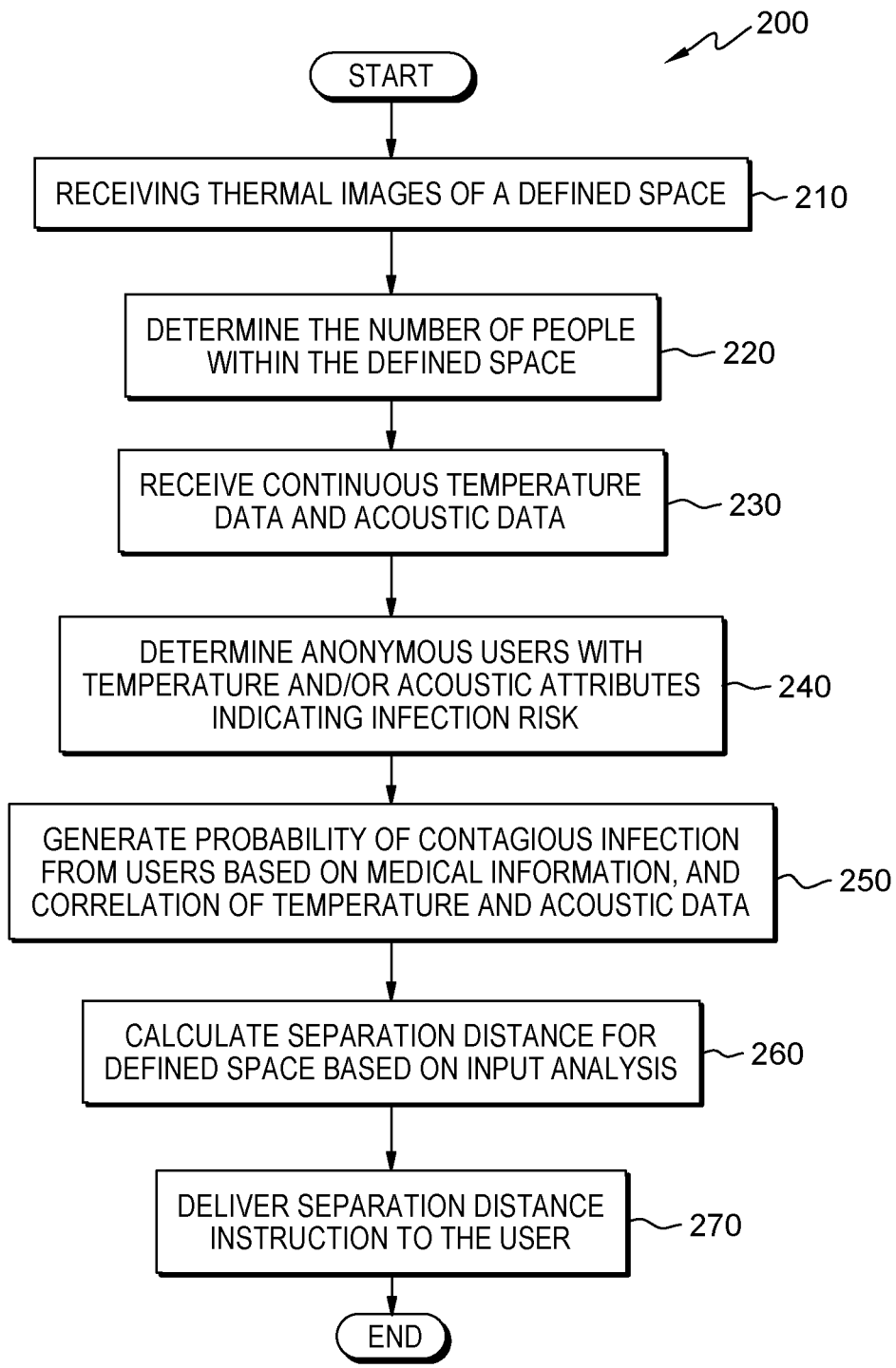
FIG. 2 is a flowchart depicting operational steps of a separation distance program operating in the distributed data processing environment of FIG. 1, in accordance with embodiments of the present invention.

FIG. 2 is a flowchart depicting operational steps of separation distance program 200, operating in distributed data processing environment 100 of FIG. 1, in accordance with embodiments of the present invention. A protected user, enabled by embodiments of the present invention, can significantly reduce exposure to transmissible disease by maintaining a specified distance between individuals in a confined space.

Separation distance program 200 receives thermal images of a defined space (step 210). In embodiments of the present invention, the positioning of thermal image sensors provides full coverage monitoring of an indoor space, also referred to herein for simplicity as the defined space. The thermal image sensors provide input data to determine a count of users within the indoor space and determine the relative location of the users within the space and with respect to each other. In some embodiments, the thermal images indicate clustering or density of users within sections of the indoor space, such as a queue or a waiting area.

For example, thermal image sensors 140 positioned on the periphery of indoor space 130 receive thermal images of users 180 and transmit the thermal image data to separation distance program 200 via network 150. The positioning of thermal image sensors 140 enables the determination of the location of users 180 between the structures of indoor space 130 dividing the space into sections or aisles.

Separation distance program 200 determines the number of people within the defined space (step 220). Each thermal image received corresponds to a respective thermal image sensor of the defined space and enables a composite view from combined thermal images that enables a count of the number of users within the defined space and a relative location of the users as the users continue to move dynamically within the space.

For example, thermal images from multiple thermal image sensors 140, positioned in an elevated perspective within indoor space 130 provide multiple viewpoints of users 180 within an aisle. Separation distance program 200 generates one or more composite images of the users 180 enabling the count of users as well as the relative location of users within indoor space 130.

Separation distance program 200 receives continuous temperature data and acoustic data (step 230). In addition to thermal image data enabling the count of the number of users and location of users within the defined space, the thermal image sensors provide continuous temperature data of the users within the defined space based on detecting the temperature of touch spots made by the users. In some embodiments, the thermal sensors may detect the temperature of users within the defined space based on exposed skin areas of the respective users. In other embodiments, the continuous temperature data of users is provided by touch-sensitive sticker devices that detect a user's temperature based on user contact with the sticker, which can be attached to handles of carts, baskets, bags, or other hand-held items used in the defined space.

Separation distance program 200 receives continuous acoustic data from acoustic sensors 160 positioned within the defined space to detect acoustic sounds from users within the defined space. Filtering techniques limit the acoustic data to include acoustic sounds corresponding to symptoms of contagious conditions of users within the defined space and exclude other detected sounds. In some embodiments, the transmission of the raw acoustic data to an acoustic filter separates the acoustic sounds and enables further transmission of symptom-like sounds such as coughing, sneezing, clearing of the throat, sniffling, and blowing of the nose, to separation distance program 200, and discards other acoustic sounds detected by the acoustic sensors. In some embodiments, the acoustic data is augmented by sounds captured by smart device microphones of users opting-in to enable separation distance program 200.

In some embodiments, an app on the respective smart device performs filtering of the acoustic sounds captured by smart device microphones, whereas in other embodiments, an acoustic filter device filters the captured acoustic data and subsequently transmits the filtered acoustic symptom-related sounds to separation distance program 200 and discards the other collected acoustic data, maintaining the anonymity of the acoustic source. In some embodiments, the source location of the symptom-based acoustic data within the defined space is determined by the intensity of the acoustic signal data from multiple acoustic sensors. The higher or highest signal intensity of acoustic sounds associated with the symptom-based sounds provided by multiple acoustic sensors indicates a source user and thermal images determine the location of the user; however, the identity of the user remains unknown, which preserves the aspect of anonymity of the users in the defined space.

For example, as users 180 move about in indoor space 130 thermal image sensors 140 capture thermal images of users 180 and transmit the images to separation distance program 200 from which a count of users 180 is determined. Additionally, the continual monitoring by thermal image sensors 140 provides dynamic input from which separation distance program 200 determines a continual count of users 180 and locations of respective users 180. Additionally, the acoustic data from users 180 within indoor space 130 becomes filtered by acoustic filter 170 and received by separation distance program 200. The acoustic data received by separation distance program 200 includes symptom-related sounds from users 180 within indoor space 130. In some embodiments, smart device microphones of opting-in users also provide acoustic data augmenting the acoustic data received from acoustic sensors 160.

Separation distance program 200 determines anonymous users with temperature and/or acoustic attributes indicating infection risk (step 240). Separation distance program 200 determines the risk level of the users within the defined space, based on the received temperature data and acoustic data associated with respective thermal images of anonymous users. Separation distance program 200 determines the number of user thermal images associated with elevated temperatures and/or symptom-related sounds as determined by the acoustic data received and determines the particular thermal image associated with users with higher infection risk attributes. The thermal image association enables separation distance program 200 to dynamically monitor the location of higher-risk users as they navigate the defined space.

For example, separation distance program 200 determines four thermal images out of the plurality of users 180 that indicate elevated temperatures and/or in addition produce sounds indicating symptoms of potential infection of contagious disease within indoor space 130, based on the thermal image data, the touch-spot data, and sticker temperature data, as well as the acoustic filtered data. Separation distance program 200 identifies the higher risk thermal images enabling monitoring of the thermal images as the users navigate through indoor space 130.

Separation distance program 200 generates a probability of contagious infection risk from users within the space, based on medical professional information and a correlation of temperature and acoustic data (step 250). Separation distance program 200 correlates the received temperature and acoustic data to the thermal images and, along with input from medical professional sources, determines a probability of contagious infection from users corresponding to the thermal images. In some embodiments, separation distance program 200 assigns a pre-determined probability of contagious infection to the thermal images of users within the defined space, based on the number of users, the area and volume of the space, the density of user locations within the defined space, the information from professional medical advisors regarding existing infections threats, and known attributes, such as ventilation. In some embodiments, the pre-determined probability is based on information from medical professional sources regarding the known methods of transmission of infection and the prevalence of infection within a geographic region. The pre-determined probability of contagious infection determines a default separation distance to be maintained to reduce exposure, which defines a radius around the protected user enabled with embodiments of the present invention.

Separation distance program 200 determines the increased probability of exposure to infection based on detection of elevated temperatures of users within the defined space, with higher elevated temperatures corresponding to a higher probability of infectious exposure. Additionally, separation distance program 200 determines an increase in the probability of exposure to infection based on the detection of symptom-like acoustic sounds. Separation distance program 200 determines higher probability levels based on higher counts and higher frequency of detected acoustic sounds.

For example, separation program 200 determines a low, medium, high, and very high probability of exposure to infection of a contagious disease, based on current professional medical information regarding prevalence of a contagious disease, the temperatures of the users within the space, the acoustic sounds corresponding to symptoms of the contagious disease, and the density and respective positions of users as determined by the thermal image sensors within the space. A low density of users with no indication of elevated temperatures and minimal or no acoustic sounds attributable to the contagious disease results in a low probability of exposure to the protected user. Alternatively in the example, a higher density of users with the indoor space, with multiple users indicating elevated temperatures and multiple thermal images of users associated with higher frequency detection of acoustic sounds corresponding to symptoms of the contagious disease results in a high or very high probability of exposure to the protected user.

Separation distance program 200 includes machine learning to detect acoustic sounds likely corresponding to symptoms of an infection such as the flu or other contagious respiratory illnesses. The training of separation distance program 200 to recognize symptom-related sounds includes the use of a plurality of samples of sounds associated with coughs, sneezes, clearing of the throat, hoarse voice, blowing of the nose, sniffling of the nose, and other acoustic sounds. The samples provide source learning data for supervised learning techniques. In some embodiments, unsupervised learning may also be performed to include non-obvious acoustic sounds associated with one or more infectious illnesses.

For example, separation distance program 200 determines a 20% probability of infectious condition of users in indoor space 130 based on information from medical professional sources and known number and density of users within indoor space 130. Separation distance program 200 determines that the thermal images of four users within indoor space 130 are associated with elevated temperatures and/or acoustic sounds. Separation distance program 200 determines that one user associated with a first thermal image has a high elevated temperature (e.g., 103° F.) and acoustic sounds of coughs attributed to the first thermal image have been detected at a high frequency. In addition, the additional acoustic sounds associated with the first thermal image include a sneeze and blowing of the nose. Separation distance program 200 determines the combination of elevated temperature and acoustic sounds associated with illness symptoms and assigns a high-risk level probability (i.e. 80-95% based on the frequency of acoustic sounds of symptoms) to the user associated with the first thermal image. A second thermal image indicates a normal temperature and positive acoustic sound detection of a cough but at a low-frequency level. Separation distance program 200 assigns a lower, but elevated probability of contagious infection (40-50%) to the user associated with the second thermal image.

Separation distance program 200 calculates a separation distance for the defined space based on the input analysis (step 260). Separation distance program 200 calculates a separation distance for the protected user considering the input data of the count of users in the defined space, the size and attributes of the defined space, the probability of contagious infection associated with the users in the defined space, and the professional medical advice and guidance available at the time. Separation distance program 200 increases the separation distance radius for the protected user, based on a higher count of users within the defined space having a higher probability of infection that is or can be contagious. In some embodiments, the professional medical advice available is used in determining an adjustment to the separation distance, such as increasing the separation distance of the protected user by 30% in sections of the defined space that includes users associated with higher infection probability but not located in the section vicinity of the protected user. In one embodiment in which separation distance program 200 determines a user with a high probability of contagious infection approaches the protected user, separation distance program 200 may instruct the protected user to maintain a separation distance that includes a 100% or higher increase. In some embodiments, separation distance program 200 may instruct a protected user to not enter the defined space, due to a determination of multiple users determined to have a high probability level of contagious infection.

Separation distance program 200, having calculated a separation distance for the protected user, and recalculated the separation distance due to movement of the protected user and other users within the space, delivers instruction of separation distance to the user (step 270). In some embodiments, separation distance program 200 delivers an instructive notification to the protected user that includes the separation distance radius to maintain between other users of the defined space. In some embodiments, separation distance program 200 dynamically indicates whether the protected user currently maintains the instructed separation distance from other users within the defined space. In some embodiments, the protected user's smart device receives delivery of an instructive notification as a text message. In other embodiments, an audible notification delivers the instructed separation distance and may further include a visual display indicating the separation distance and whether the protected user currently maintains the separation distance. In some embodiments, the notification may instruct the protected user to not enter the defined space due to a very high probability of contagious infection among multiple users within the defined space.

In some embodiments of the present invention, the instructive notification may be a haptic, audio, or visible warning alert that the protected user is approaching the dynamically calculated separation distance, and a distinct alert is delivered to the protected user (haptic, audio, visual, or combinations) when the separation distance is violated.

Figure 3:
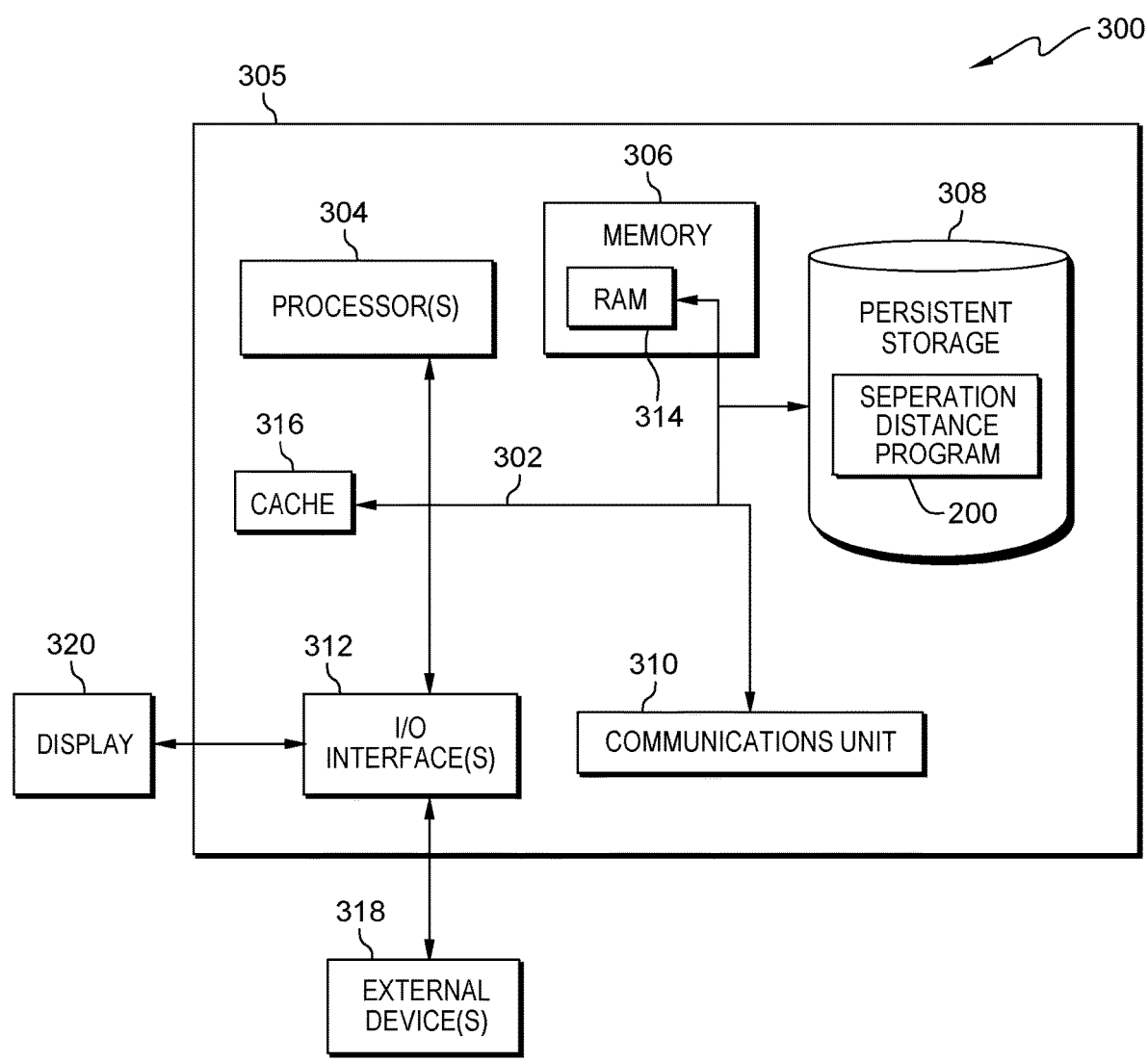
FIG. 3 depicts a block diagram of components of a computing system, including a computing device configured to operationally perform the separation distance program of FIG. 2, in accordance with an embodiment of the present invention.

FIG. 3 depicts a block diagram of components of a computing system, including computing device 305, configured to include or operationally connect to components depicted in FIG. 1, and with the capability to operationally perform separation distance program 200 of FIG. 3, in accordance with an embodiment of the present invention.

Computing device 305 includes components and functional capability similar to components of computing device 110, (FIG. 1), in accordance with an illustrative embodiment of the present invention. It should be appreciated that FIG. 3 provides only an illustration of one implementation and does not imply any limitations with regard to the environments in which different embodiments may be implemented. Many modifications to the depicted environment may be made.

Computing device 305 includes communications fabric 302, which provides communications between computer processor(s) 304, memory 306, persistent storage 308, communications unit 310, an input/output (I/O) interface(s) 312. Communications fabric 302 can be implemented with any architecture designed for passing data and/or control information between processors (such as microprocessors, communications, and network processors, etc.), system memory, peripheral devices, and any other hardware components within a system. For example, communications fabric 302 can be implemented with one or more buses.

Memory 306, cache memory 316, and persistent storage 308 are computer-readable storage media. In this embodiment, memory 306 includes random access memory (RAM) 314. In general, memory 306 can include any suitable volatile or non-volatile computer-readable storage media.

In one embodiment, separation distance program 200 is stored in persistent storage 308 for execution by one or more of the respective computer processors 304 via one or more memories of memory 306. In this embodiment, persistent storage 308 includes a magnetic hard disk drive. Alternatively, or in addition to a magnetic hard disk drive, persistent storage 308 can include a solid-state hard drive, a semiconductor storage device, read-only memory (ROM), erasable programmable read-only memory (EPROM), flash memory, or any other computer-readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer-readable storage medium that is also part of persistent storage 308.

Communications unit 310, in these examples, provides for communications with other data processing systems or devices, including resources of distributed data processing environment 100. In these examples, communications unit 310 includes one or more network interface cards. Communications unit 310 may provide communications through the use of either or both physical and wireless communications links. Separation distance program 200 may be downloaded to persistent storage 308 through communications unit 310.

I/O interface(s) 312 allows for input and output of data with other devices that may be connected to computing system 300. For example, I/O interface 312 may provide a connection to external devices 318 such as a keyboard, keypad, a touch screen, and/or some other suitable input device. External devices 318 can also include portable computer-readable storage media such as, for example, thumb drives, portable optical or magnetic disks, and memory cards. Software and data used to practice embodiments of the present invention, e.g., separation distance program 200 can be stored on such portable computer-readable storage media and can be loaded onto persistent storage 308 via I/O interface(s) 312. I/O interface(s) 312 also connects to a display 320.

Display 320 provides a mechanism to display data to a user and may, for example, be a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source code or object code written in any combination of one or more programming languages, including an object-oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer-readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for dynamically determining a separation distance, the method comprising:
   receiving, by one or more processors, thermal images of a space of pre-determined dimensions, wherein the thermal images indicate a count and location of a plurality of users within the space;
   receiving, by the one or more processors, temperature data of respective users of the plurality of users within the space measured via thermal measurement devices positioned to detect the temperature of the respective users in the space;
   receiving, by the one or more processors, acoustic data from the respective users within the space, wherein the acoustic data is filtered via a filtering model trained using artificial intelligence to include specific symptom-related sounds and discard other sounds;
   generating, by the one or more processors, a probability of a contagious risk presented by a first user of the respective users within the space, based on medical professional information and correlating a temperature of the first user and the acoustic data associated with the first user;
   generating, by the one or more processors, one or more composite images of the respective users based on the thermal images enabling the count of the plurality of users and the location of users;
   calculating, by the one or more processors, a separation distance for a protected user to maintain from the first user within the space, based on the probability of the contagious risk of the first user, a location of the protected user, and a location of the first user within the space;
   delivering to the protected user, by the one or more processors, a notification corresponding to the calculated separation distance to maintain from the first user within the space; and
   assigning the probability of the contagious risk to the one or more composite images of the respective users within the space, based on the count of the plurality of users, an area and volume of the space of pre-determined dimensions, and a density of user locations within the space of pre-determined dimensions.

2. The method of claim 1, wherein the temperature data of the respective users within the space includes receiving the temperature data from one or more temperature-sensing stickers attached to a handle held by the respective users.

3. The method of claim 1, wherein the temperature data and the acoustic data associated with a location of a user within the space is anonymously associated with a thermal image of the user in closest proximity to a microphone detecting the acoustic data.

4. The method of claim 1, wherein the acoustic data is augmented by acoustic signals detected by microphones of smart devices of the respective users within the space and which is transmitted to the filtering model trained using artificial intelligence to filter specific symptom-related sounds and discard other sounds.

5. The method of claim 1, wherein the specific symptom-related sounds include one or a combination of the group consisting of a cough, a sneeze, a sniffle, a clearing of a throat, and a blowing of a nose and wherein the one or more composite images comprise combined thermal images.

6. The method of claim 1, wherein the separation distance is configured by an administrative role user and based on current professional medical advice and determined conditions of user density, the probability of the contagious risk presented by the first user, and proximity of the first user and the respective users to the protected user within the space, the method further comprising adjusting the separation distance based on input data received comprising the count of the plurality of users within the space, a location of users within sections of the space, a probability of contagious infection determined by the medical professional information of presently known infectious disease, and detection of temperature and acoustic signals indicating potential infectious disease symptoms from specific users and the location of the users within the space.

7. A computer program product for dynamically determining a separation distance, comprising:
one or more computer-readable storage media and program instructions stored on the one or more computer-readable storage media, the program instructions comprising:
program instructions to receive thermal images of a space of pre-determined dimensions, wherein the thermal images indicate a count and location of a plurality of users within the space;
program instructions to receive, by the one or more processors, temperature data of respective users of the plurality of users within the space measured via thermal measurement devices positioned to detect the temperature of the respective users in the space;
program instructions to receive acoustic data from the respective users within the space, wherein the acoustic data is filtered via a filtering model trained using artificial intelligence to include specific symptom-related sounds and discard other sounds;
program instructions to generate a probability of a contagious risk presented by a first user of the respective users within the space, based on correlating a temperature of the first user and the acoustic data associated with the first user;
program instructions to generate one or more composite images of the respective users based on the thermal images enabling the count of users and the location of users;
program instructions to calculate a separation distance for a protected user to maintain from the first user within the space, based on the probability of the contagious risk of the first user, a location of the protected user, and a location of the first user within the space;
program instructions to deliver to the protected user a notification corresponding to the calculated separation distance to maintain from the first user within the space; and
assigning the probability of the contagious risk to the one or more composite images of the respective users within the space, based on the count of users, an area and volume of the space of pre-determined dimensions, and a density of user locations within the space of pre-determined dimensions.

8. The computer program product of claim 7, wherein the temperature data of the respective users within the space includes receiving the temperature data from one or more temperature-sensing stickers attached to a handle held by the respective users.

9. The computer program product of claim 7, wherein thermal measurement devices are positioned to detect the temperature of users in the space.

10. The computer program product of claim 7, wherein the temperature data and the acoustic data associated with a location of a user within the space is anonymously associated with a thermal image of the user.

11. The computer program product of claim 7, wherein the acoustic data is augmented by acoustic signals detected by microphones of smart devices of the respective users within the space.

12. The computer program product of claim 7, wherein the specific symptom-related sounds includes one or a combination of the group consisting of a cough, a sneeze, a sniffle, a clearing of a throat, and a blowing of a nose.

13. The computer program product of claim 7, wherein the separation distance is configured by an administrative role user and based on current professional medical advice and determined conditions of user density, the probability of the contagious risk presented by the first user, and proximity of the first user and the respective users to the protected user within the space.

14. A computer system for dynamically determining a separation distance, comprising:
one or more computer processors;
one or more computer-readable storage media;
program instructions stored on the one or more computer-readable storage media, the program instructions comprising:
program instructions to receive thermal images of a space of pre-determined dimensions, wherein the thermal images indicate a count and location of a plurality of users within the space;
program instructions to receive temperature data of respective users of the plurality of users within the space measured via thermal measurement devices positioned to detect the temperature of the respective users in the space;
program instructions to receive acoustic data from the respective users within the space, wherein the acoustic data is filtered via a filtering model trained using artificial intelligence to include specific symptom-related sounds and discard other sounds;
program instructions to generate a probability of a contagious risk presented by a first user of the respective users within the space, based on correlating a temperature of the first user and the acoustic data associated with the first user;

program instructions to generate one or more composite images of the respective users based on the thermal images enabling the count of users and the location of users;

program instructions to calculate a separation distance for a protected user to maintain from the first user within the space, based on the probability of the contagious risk of the first user, a location of the protected user, and a location of the first user within the space;

program instructions to deliver to the protected user a notification corresponding to the calculated separation distance to maintain from the first user within the space; and assigning the probability of the contagious risk to the one or more composite images of the respective users within the space, based on the count of users, an area and volume of the space of pre-determined dimensions, and a density of user locations within the space of pre-determined dimensions.

15. The computer system of claim 14, wherein the temperature data of the respective users within the space includes receiving the temperature data from one or more temperature-sensing stickers attached to a handle held by the respective users.

16. The computer system of claim 14, wherein the temperature data and the acoustic data associated with a location of a user within the space is anonymously associated with a thermal image of the user.

17. The computer system of claim 14, wherein the acoustic data is augmented by acoustic signals detected by microphones of smart devices of the respective users within the space.

18. The computer system of claim 14, wherein the specific symptom-related sounds include one or a combination of the group consisting of a cough, a sneeze, a sniffle, a clearing of a throat, and a blowing of a nose.

19. The computer system of claim 14, wherein the separation distance is configured by an administrative role user and based on current professional medical advice and determined conditions of user density, the probability of the contagious risk presented by the first user, and proximity of the first user and the respective users to the protected user within the space.

* * * * *